United States Patent [19]

Wentzell et al.

[11] Patent Number: 4,532,808
[45] Date of Patent: Aug. 6, 1985

[54] CORNER REGION ULTRASONIC INSPECTION DEVICE

[75] Inventors: Timothy H. Wentzell, South Windsor; Mark V. Brook, West Hartford, both of Conn.

[73] Assignee: Combustion Engineering, Inc., Windsor, Conn.

[21] Appl. No.: 541,406

[22] Filed: Oct. 13, 1983

[51] Int. Cl.³ ............... G01N 29/04; G21C 17/00
[52] U.S. Cl. ........................... 73/640; 73/634; 73/635; 73/637; 376/249
[58] Field of Search ............... 376/249; 73/633, 634, 73/635, 637, 640

[56] References Cited

U.S. PATENT DOCUMENTS 3,863,496  2/1975  Hiramatsu et al. ............ 73/634
4,117,733  10/1978  Gugel ............................ 376/249

FOREIGN PATENT DOCUMENTS 2634158  2/1978  Fed. Rep. of Germany ........ 73/633

Primary Examiner—Howard A. Birmiel
Attorney, Agent, or Firm—Troxell K. Snyder

[57] ABSTRACT

A method and device for ultrasonically inspecting the corner region formed by the joining of a pair of cylindrical conduits is disclosed. Ultrasonic sound beams (62) are transmitted beneath inner surface (12) of the first conduit at an oblique angle resulting in a shallow refracted sound path (74) through the solid corner region (84). Sound energy (76) reflected by the presence of a radially oriented crack (67) within the desired zone of interest (66) passes (80) out of the solid (84) for detection. A device having an ultrasonic transmitter (44) and a directional receiver (60) is disclosed carrying out the inspection method according to the present invention.

7 Claims, 5 Drawing Figures

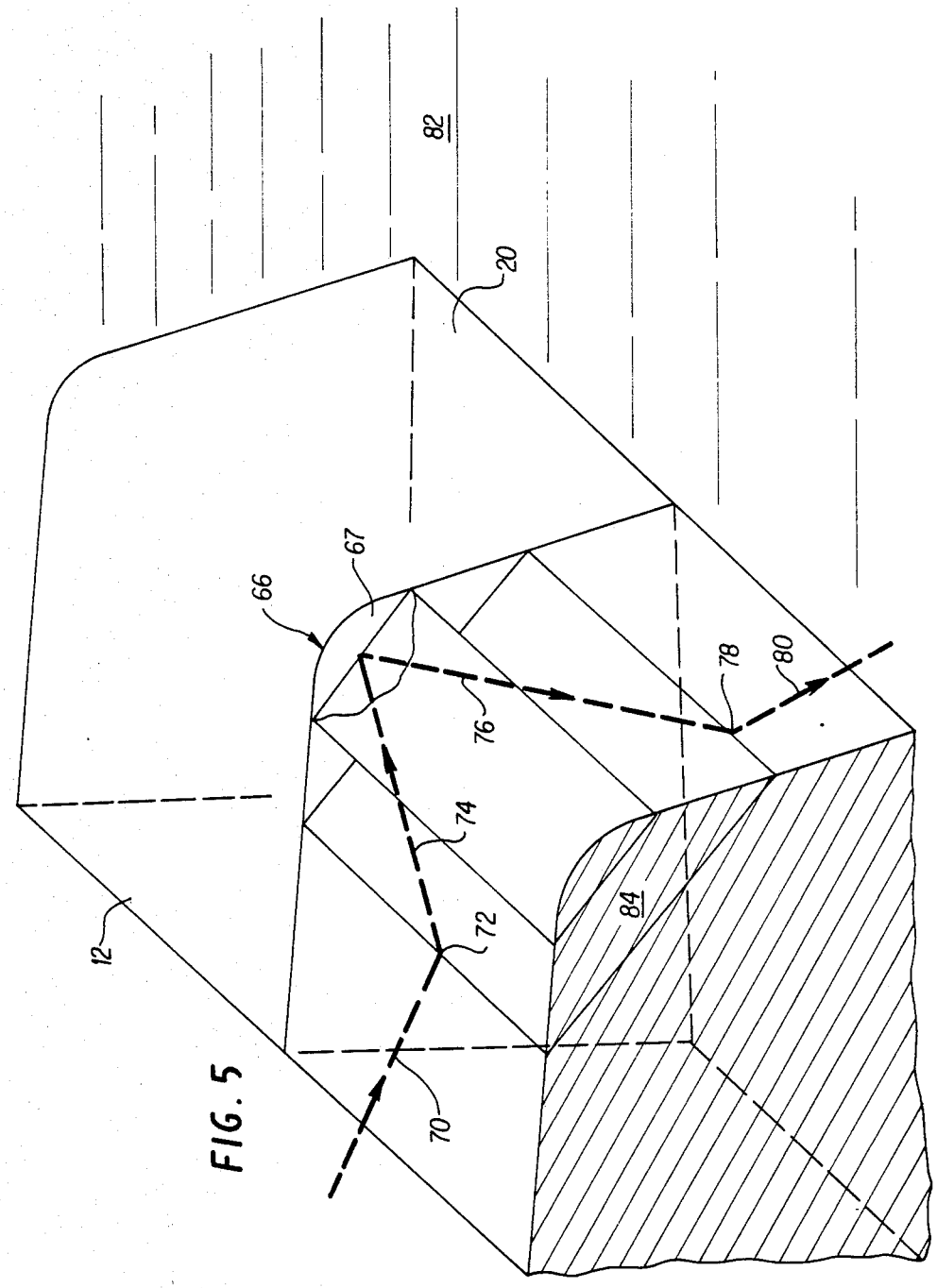

CORNER REGION ULTRASONIC INSPECTION DEVICE

FIELD OF THE INVENTION

The present invention pertains to a device and method for performing a nondestructive, ultrasonic examination and, more particularly, to a device and method for performing a nondestructive, ultrasonic examination beneath the surface of a corner region.

BACKGROUND OF THE INVENTION

The use of nondestructive inspection techniques to evaluate the condition of solid structures is well known, particularly in those situations where ultrasonic sound beams are directed beneath a solid surface for the detection of cracks or voids therein. In performing ultrasonic inspection beneath the surface of an object, a beam of ultrasonic sound energy is directed downward into the solid body such that the transmitted beam will pass through a zone of interest in which the presence of any flaws is to be determined. Should a flaw exist within this zone of interest, the ultrasonic sound beam will be reflected by the flaw and be detected by a properly positioned directional receiver or microphone located outside of the solid body. By properly positioning the sound transmitter and directional receiver, it is possible to restrict the size of the zone of interest in which the presence of flaws will cause ultrasonic sound energy to be reflected to the receiver.

One industry in which this type of limited inspection is desirable is the nuclear power industry.. Nuclear reactor vessels are typically fabricated from a base material such as carbon steel and coated with a cladding of stainless or other temperature and radiation resistant material. For a clad pressure vessel, the presence of any flaws or cracks in the base material or cladding is detrimental to the functionality and safety of the vessel. As a reflection of the importance of this factor, governmental regulatory agencies charged with the supervision of the nuclear power industry have required that inspection techniques used not only during the construction of the vessels, but also for the in-service inspection of operating reactors, include a thorough inspection of the region beneath inner cladding in the base material, as well as the cladding itself.

A number of ultrasonic inspection devices have been developed and are in use which concentrate on the zone of interest which includes the cladding and the base material just beneath it. As discussed above, this limitation is achieved by properly positioning the ultrasonic sound transmitter and directional receiver in relation to the solid body undergoing inspection. As the greater part of the clad vessel is of a regular geometric shape, i.e., cylindrical or spherical, it has been relatively straightforward to develop the ultrasonic inspection devices for detecting flaws. However, there exists one portion of the reactor vessel wherein the geometric shape is not constant. This area is the junction between the coolant flow nozzles and the reactor vessel. This junction, in reality the intersection of a large vertical cylinder and a small horizontal cylinder, produces a saddle-shaped corner region wherein the angle of the corner can vary from 90° to approximately 130°, dependent upon the radial displacement about the axis of the small horizontal cylinder, or coolant nozzle.

Due to the variable geometry. of this section, inspection techniques heretofore used or proposed have succeeded in only approximate inspections of this potentially critical region, or have required the use of multiple ultrasonic transmitters and directional receivers in order to thoroughly perform the desired inspection. See assignee's co-pending application, Ser. No. 503,978, filed June 13, 1983 which discloses a corner region inspection device utilizing a plurality of ultrasonic transmitters and directional receivers for accommodating the variable geometry of the nozzle corner region.

While multiple transmitters and receivers have proved effective, the use of such systems requires the operator to continually monitor the radial displacement of the inspection device for the purpose of determining which transmitter-receiver combination is currently operable for inspecting the cladding and interface. Moreover, those devices currently proposed or in use must be moved along a saddle-shaped path which corresponds to the shape of the nozzle-vessel intersection. Such movement requires relatively complex control of the arm mechanism which remotely manipulates the inspection devices within the reactor vessel. What is required is an ultrasonic inspection device for examining a zone of interest within the variable geometry. corner region, such as is found in a nuclear reactor vessel, which is self-aligning so as to not reouire exact or very complex motion of the instrument manipulator arm.

SUMMARY OF THE INVENTION

The present invention is directed to a device for inspecting the region beneath a corner formed by the intersection of two surfaces. A pair of ultrasonic transducers, one for transmitting ultrasonic sound energy and one for directionally receiving ultrasonic sound energy, are each mounted on separate carriages joined by a pivoted arm. Each carriage is positioned in relation to the corner by at least one roller which contacts the respective surface. During the inspection process, the device is moved over the corner region by a manipulator arm or boom which keeps the rollers in contact with the surfaces. One transducer is slidably mounted on its respective carriage and is translated along the mount under the influence of the pivoted arm, thus maintaining a fixed distance from the apex of the corner.

The device according to the present invention is particularly useful in inspecting a zone of interest located beneath the surface of the variable geometry corner region formed by the right intersection of two cylindrical pressure conduits, or vessels, of different inner diameters, such as is formed by the coolant nozzle in a nuclear reactor vessel. In this application, the action of the sliding transducer mount and the pivoted arm allows the device to traverse the saddle-shaped corner region while accurately maintaining the transmitting and receiving transducers in an optimum orientation with respect to the corner region.

It is a further feature of the device according to the present invention that the manipulator arm need not be moved in a complex fashion in order to accommodate the saddle-shape of the corner region. The action of the sliding mount and pivoted arm allow the manipulator arm to traverse a simple circular path about the radius of the nozzle without requiring reciprocating motion along the nozzle axis.

It is a still further feature of the device according to the present invention that the transmitter may be skewed out of the plane of the axes of the cylinders so as to detect radially oriented cracks within the zone of interest.

BRIEF DESCRIPTION OF THE DRAWING FIGURES

FIG. 5 shows an isometric schematic detailing the skewing of the ultrasonic beams within the inspected solid.

DESCRIPTION OF THE PREFERRED EMBODIMENT

Figure 1:
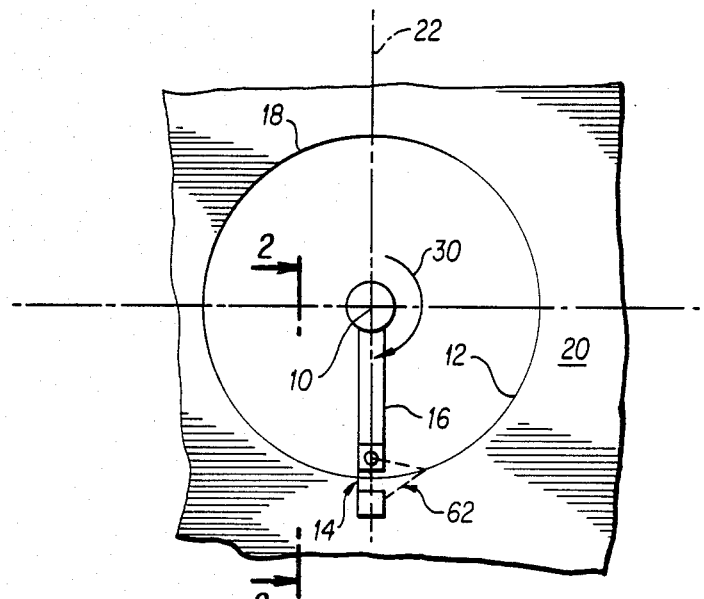
FIG. 1 shows a partial view of the device and manipulator arm as positioned within the bore of the nozzle.

FIG. 1 shows a view down the bore of a coolant nozzle from a point within a nuclear reactor vessel. The nozzle axis 10 and the nozzle inner surface 12 are indicated on the drawing figure. The inspection device according to the present invention is shown 14 affixed to the end of a manipulator arm 16 and is in contact with the corner region 18 formed by the intersection of the nozzle 12 and the vessel 20.

During inspection, the manipulator boom 16 rotates about the nozzle axis 10 thus moving the inspection device 14 in a generally circular path over the corner region 18. For the purposes of further discussion, the angular displacement of the inspection device about the nozzle axis 10 is determined by using the upward extending vertical line 22 as the 0° reference angle. The manipulator boom 16 and inspection device 14 are therefore shown in FIG. 1 as being at an angular displacement of 180°.

Figure 2:
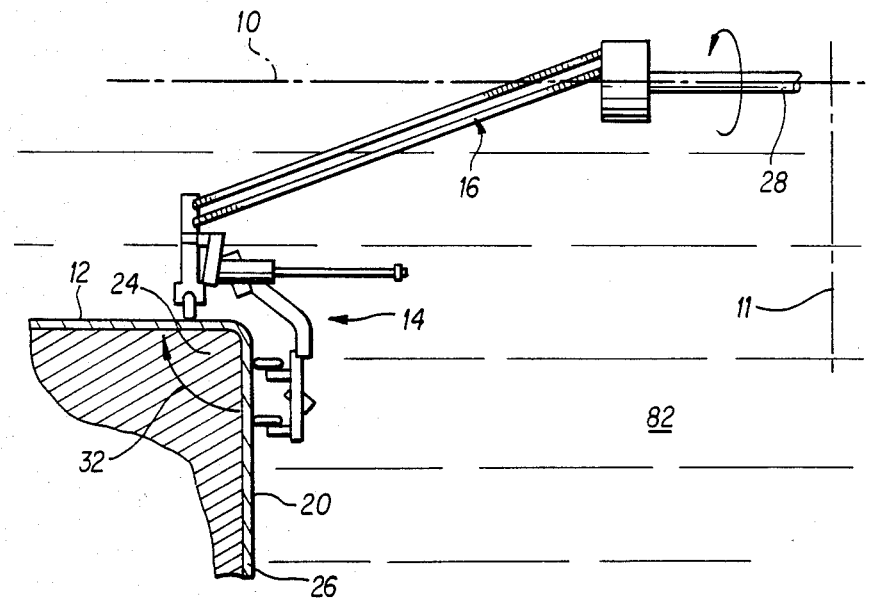
FIG. 2 shows a side view in the plane of the nozzle and vessel axes of the device according to the present invention.

FIG. 2 shows the indicated side view of the device 14 and the manipulator arm 16. The nozzle inner surface 12 and the vessel inner surface 20 are shown along a cross section of the corner region formed by the intersection of these two surfaces. The central axis 10 of the nozzle and the central axis 11 of the vessel are shown intersecting in the plane of the drawing at a right angle. The corner region consists of a base material 24 covered by a layer of cladding material 26. For the reactor vessel of a nuclear power plant, the base material 24 is typically carbon steel for cost and fabrication considerations, while the cladding 26 is typically a stainless steel to provide resistance to radiation and corrosion.

The manipulator boom 16 is of a type generally used in this industry for the positioning of inspection devices within the reactor core. The manipulator shown in FIG. 2 is oriented with respect to the nozzle axis 10 so that simple rotation of the boom section 28 will cause the inspection device 14 to traverse a circle about the nozzle axis 10.

The locus of points described by the right intersection of two cylindrical conduits of differing inner diameters does not fall within one plane. This locus of points describes a "saddle-shape" wherein the linear displacement of the intersection locus along the nozzle axis 10 is dependent upon the angular displacement 30 of the locus point about that same nozzle axis 10. Not only does the linear displacement along the nozzle axis 10 change with angular displacement 30, but the included angle between the nozzle inner surface 12 and the vessel inner surface 20 is also a variable, dependent upon the angular displacement 30. At angular displacements of 0° and 180°, the included angle 32 is 90° for the right intersection of two cylinders, i.e., the central axes 10, 11 of the cylinders meet at a right angle.

The included angle 32 reaches its greatest magnitude at angular displacements 30 of 90° and 270°, with the actual value being dependent upon the relative diameters of the two cylinders. If, for example, the nozzle 12 diameter is equal to that of the vessel 20 diameter, the included angle at the 90° and 270° angular displacement 30 would be 180°. If, on the other hand, the diameter of the vessel 20 is very much larger in diameter than the nozzle 12, the included angle 32 will approach a minimum value of 90° at these two angular displacements.

The accommodation of this variation in the included angle 32 is an important and necessary feature of any corner region inspection device. In ultrasonic inspection devices, this must be accomplished by variation of the relative position of the individual transducers relative to the surfaces of the body being inspected. As far as Applicants are aware, the existing inspection devices, although able to change the angular orientation of the transducers with respect to the surfaces 12, 20, require a plurality of ultrasonic transmitters and receivers to effectively inspect the entire corner region 18.

Figure 3:
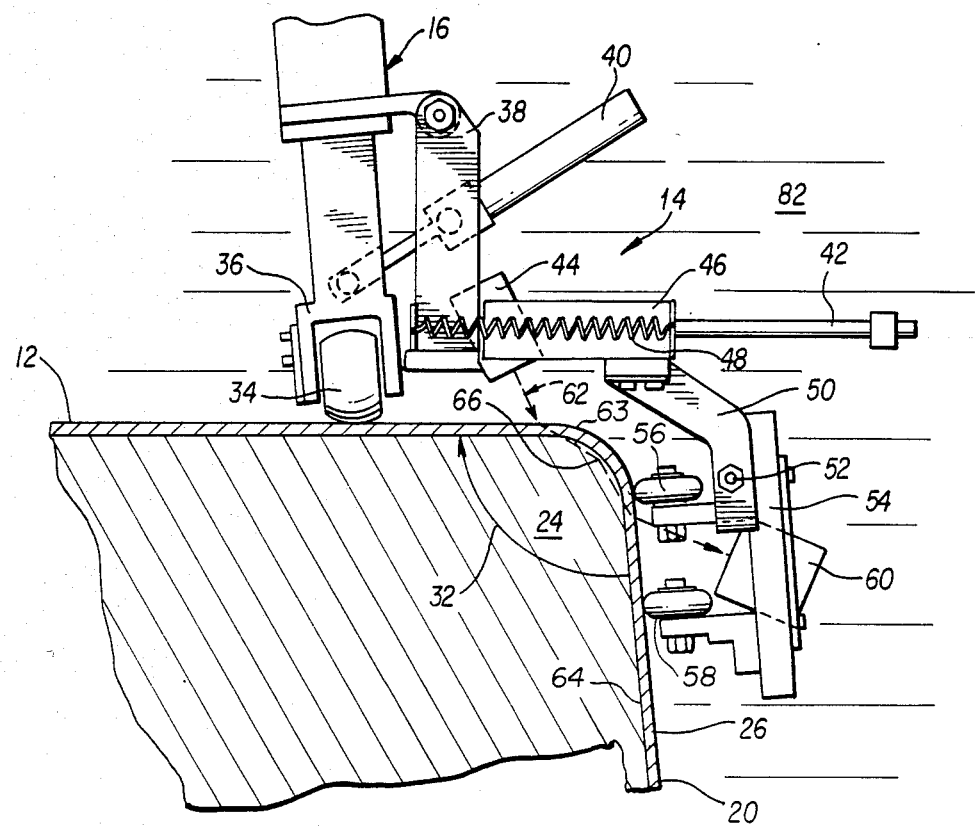
FIG. 3 shows a detailed side view of the device at the 180° angular displacement.

FIG. 3 shows a more detailed representation of the inspection device according to the present invention. The device consists of a first carriage, including a nozzle roller 34, a nozzle roller yoke 36, a swing arm 38, a hydraulic actuator 40, and a carriage slide 42. During inspection, the nozzle roller yoke 36 and the swing arm 38 are maintained in contact as shown in FIG. 3. During insertion and removal of the inspection device 14, the hydraulic actuator, or any other suitable actuation means 40, operates to separate the swing arm 38 and the nozzle roller yoke 36 to facilitate the manipulation of the device 14.

An ultrasonic transmitter 44 is secured to a slider 46 which cooperates with the carriage slide 42 to permit linear translation of the transmitter 44 along the carriage slide 42. A spring 48, or other means, urges the slider 46, and therefore the ultrasonic transmitter 44, along the carriage slide 42 in the direction of the nozzle roller 34. During inspection, the vessel and nozzle are filled with a liquid medium 82, usually water, which both controls radiation from the vessel and reactor internals and allows transmission of the ultrasonic sound energy to and from the transducers 44, 60.

A pivot arm 50 is shown rigidly secured to the slider 46 and extending both outward and downward therefrom. This pivot arm 50 terminates in its free end in a pivot 52 whereby a second carriage 54 is attached.

The second carriage 54 includes at least two vessel rollers 56, 58 which serve to properly position the second carriage at a fixed distance from the vessel inner surface 20 and to orient the second carriage 54 with respect thereto. A directional ultrasonic receiver 60, secured to the second carriage 54, completes the inspection device according to the present invention.

With reference still to FIG. 3, it can be seen that during inspection, the ultrasonic transmitter 44 is slidably aounted to the first carriage assembly 34, 36, 38, 42, which is maintained at a fixed spacing above the nozzle inner surface 12 by the action of the nozzle roller 34. A beam of ultrasonic sound energy 62 originates from the ultrasonic transmitter 44, travels through the medium 82, and passes beneath the nozzle surface 12 into the cladding layer 26. The ultrasonic sound beam is shown in FIG. 3 as passing through the interface 64 between the cladding 26 and the base material 24. The occurrence of a crack, void, separation, or other flaw within the zone of interest 66 swept by the ultrasonic sound beam 62, will disrupt the progession of the sound beam 62 and the result is recognizable as a fluctuation of the sound waves received by the directional ultrasonic receiver 60. The technology for interpreting the meaning of the ultrasonic sound waves received is known in the art of ultrasonic testing and will not be detailed herein. It is sufficient to say that the detected variations will occur either in the magnitude of the received signal or other characteristics which may be detected or otherwise observed by an operator remote to the inspecting apparatus.

As can be seen from FIG. 3, the orientation of the ultrasonic transmitter 44, with respect to the nozzle inner surface, is maintained by the action of the carriage slide 42 and the slider 46. The orientation of the receiver 60, with respect to the vessel inner surface 20, is maintained by the action of the vessel rollers 56, 58. It is still further apparent from drawing FIG. 3, that the distances from the transmitter 44 to the apex of the corner 63 and from the apex 63 to the receiver 60 is maintained by the pivot arm 50 by virtue of its connection to the slider 46 and the pivot 52.

The manipulator arm 16 forces the nozzle roller 34 into contact with the nozzle inner surface 12, while the spring means 48 tensions the vessel rollers 56, 58 against the vessel inner surface 20 by acting through the pivot arm 50, the pivot 52, and the second carriage 54.

During inspection with a device according to the present invention, the manipulator arm 16 is rotated simply about the nozzle axis 10. The nozzle roller 34, and hence the entire first carriage assembly, thus describes a circular path about the inner nozzle surface 12. As also discussed above, the saddle-shape area under inspection does not describe a simple circular locus of points, but rather a saddle-shape which includes a linear translation along the nozzle axis 10. The inspection device according to the present invention accommodates this linear variation, as well as changes in the angle 32 included between the nozzle inner surface 12 and the vessel inner surface 20, in a manner which will herein be disclosed with further reference to FIG. 4.

Figure 4:
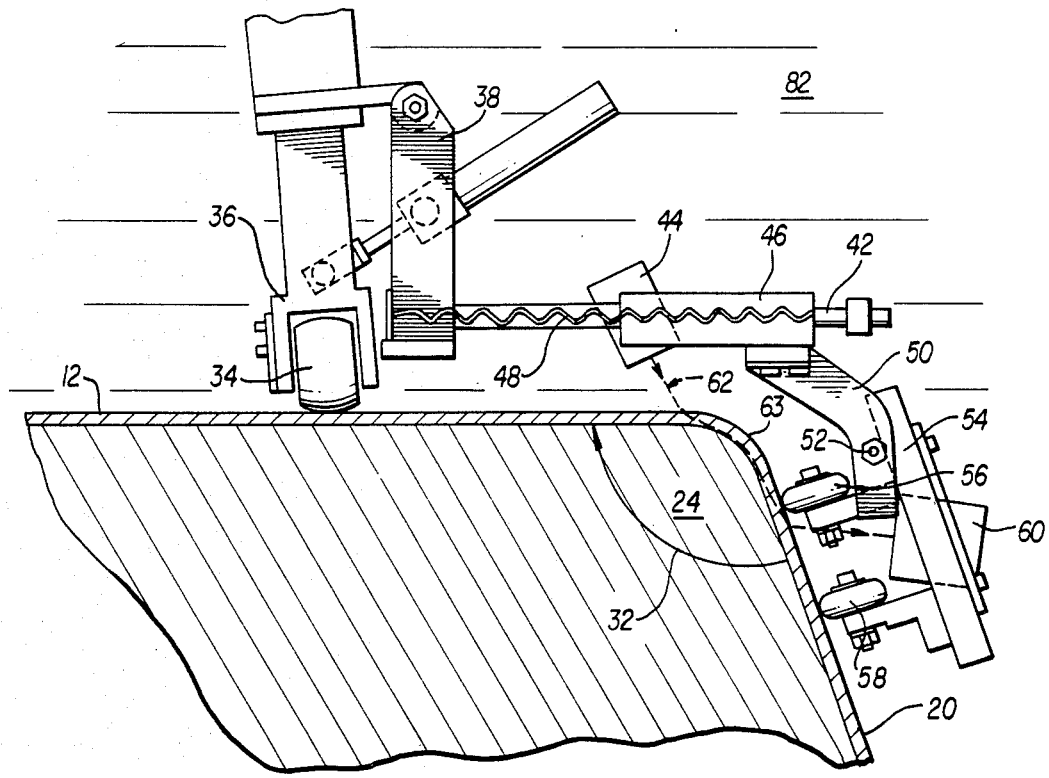
FIG. 4 shows the device at the 90° or 270° displacement.

FIG. 4 shows the device according to the present invention at a radial displacement other than 0° or 180°. In comparison with FIG. 3, the corner region of FIG. 4 has translated substantially toward the interior of the vessel 20, and the included angle 32 between the nozzle inner surface 12 and the vessel inner surface 20 is of substantially greater magnitude. These changes are accommodated by the device according to the present invention in two ways: first, the change in the included angle 32 results in a rotation of the second carriage 54 about the pivot 52 due to the action of the vessel rollers 56, 58 which contact the vessel inner surface 20. The directional ultrasonic receiver 60 is therefore maintained at the same angular orientation with respect to the vessel inner surface 20. Secondly, the linear movement of the corner region along the nozzle axis 10 has been accommodated by translation of the slider 46 along the carriage slide 42 under the influence of the pivot arm 50 and the second carriage 54. Both ultrasonic transducers 44, 60 thus are maintained at a constant separation distance from the corner apex 62 despite the linear movement and variable internal angle of the corner region 24.

By maintaining the above-described separation of the ultrasonic transducers 44, 60, as well as the orientation of each individual transducer 44, 60 to its respective surface 12, 20, the inspection device according to the present invention permits the complete inspection of the zone of interest 66 within the corner region of the inner section of two cylindrical surfaces 12, 20 with only one ultrasonic transmitter and one directional ultrasonic receiver. The device also simplifies the motion of the manipulator arm 16, by not requiring the manipulator arm 16 to translate the inspection device along the nozzle axis 10 in order that the inspection device might accurately track the saddle-shaped corner region being inspected.

Still one other feature of the device according to the present invention is shown to complete the disclosure of the preferred embodiment. Referring back to FIG. 1, a pair of sound beams 62 are shown in the figure as traveling out of the plane formed by the manipulator arm 16 and the inspection device 14. By orienting the ultrasonic transducers 44, 60 so as to transmit and receive ultrasonic sound energy in a direction skewed out of the plane depicted in FIGS. 2, 3, and 4, the inspection of the corner region is rendered more accurate and thorough by permitting the detection of radially extending cracks within the corner region. As will further be appreciated by those skilled in the art of ultrasonic inspection, the skewing of the transmitted ultrasonic beam results in no significant ultrasonic energy being received by the directional receiver when the ultrasonic sound energy passes through the zone of interest without encountering any flaws or other disturbances. The detection of significant reflected ultrasonic energy by the directional receiver, oriented to receive only ultrasonic sound energy originating within the zone of interest, simplifies the analysis and flaw detection procedure used by the remote operator.

This feature is disclosed schematically in FIG. 5. Transmitted ultrasonic sound beam 70 obliquely strikes the nozzle inner surface 12 at point 72 and passes into the solid corner region 84. In passing from the medium 82, usually water, surrounding the inspection device and nozzle intersection into the solid, the sound beam 70 is refracted along a shallow path 74 which passes through the zone of interest 66 located near the surface of the corner region 84. A radial crack 67, within the zone 66, causes reflection of the transmitted beam 74 along a return path 76 which passes out of the solid body at point 78 in the vessel surface 20. Surface refraction again alters the path of this sound beam which is shown 80 as traveling out of the solid through the immersing medium 82.

These and other advantages of the present invention will be apparent to those skilled in the art upon thorough inspection of the preceding specification and the appended claims and drawing figures.

We claim:

1. A device for detecting flaws within a solid corner region formed by the intersection of a pair of solid members having a first surface and a second surface meeting at a corner point, comprising:
   a first carriage, movable over the first surface of the corner region proximate the corner point, including means for maintaining the first carriage at a fixed distance above the first surface;

a first ultrasonic transducer, slidably mounted on the first carriage, for transmitting ultrasonic sound energy into a specific zone of interest beneath the surface of the corner region;

a pivot arm, rigidly secured at one end to the first transducer, extending at least partially around the corner point, and including a pivot in the unsecured end;

a second carriage, attached to the arm at the pivot and freely movable thereabout, including means for maintaining the second carriage a fixed distance and orientation with respect to the second surface; and a second ultrasonic transducer, secured to the second carriage, for receiving ultrasonic sound energy reflected by any material flaws present within the zone of interest.

2. The device as recited in claim 1, further comprising a movable manipulator arm, secured to the first carriage, for manipulating the device over the corner region to be inspected.

3. The device as recited in claim 2, wherein the corner region is formed by the intersection of two cylindrical conduits and the first and second surfaces are the interior surfaces of corresponding first and second conduits.

4. The device as recited in claim 3, wherein the first conduit has a significantly smaller inner diameter than the second conduit, and the manipulator arm rotates within the first conduit for moving the device over the entire corner region formed by the surfaces.

5. The device as recited in claim 1, wherein the means for maintaining the first carriage at a fixed distance above the first surface comprises a nozzle roller contacting the first surface and wherein the means for maintaining the second carriage at a fixed distance and orientation with respect to the second surface further comprises a pair of vessel rollers contacting the second surface.

6. The device as recited in claim 3, wherein the first and second transducers are oriented to respectively direct and receive ultrasonic sound energy into and from the corner region beneath the first and second surfaces at directions skewed out of a plane defined by the axes of the first and second conduits.

7. A method for detecting radially oriented cracks beneath the corner region formed by the intersection of two cylindrical conduits, comprising the steps of:

transmitting a beam of ultrasonic sound energy into the corner region at an angle oblique to the inner surface of the first conduit and skewed with respect to the plane defined by the centerlines of the first and second conduits, and directionally monitoring the surface of the second conduit for detecting the presence of reflected ultrasonic sound energy reflected by radially oriented cracks present within the corner region.

* * * * *